US00PP12969P2

(12) United States Plant Patent
van Gaalen

(10) Patent No.: US PP12,969 P2
(45) Date of Patent: Sep. 17, 2002

(54) PHLOX PLANT NAMED 'EMPTY FEELINGS'

(75) Inventor: Irenaeus Antonius Maria van Gaalen, Den Hoorn (NL)

(73) Assignee: R. van Gaalen, B.V., Den Hoorn (NL)

( * ) Notice: Subject to any disclaimer, the term of this patent is extended or adjusted under 35 U.S.C. 154(b) by 39 days.

(21) Appl. No.: 09/844,365

(22) Filed: Apr. 30, 2001

(51) Int. Cl.[7] ..... A01H 5/00
(52) U.S. Cl. ..... Plt./326
(58) Field of Search ..... Plt./320

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Phlox plant named 'Empty Feelings', characterized by its upright plant habit; dark green leaves; and panicles of dark red bract-like structures.

1 Drawing Sheet

BACKGROUND OF THE INVENTION

The present Invention relates to a new and distinct cultivar of Phlox plant, botanically known as *Phlox paniculata,* and hereinafter referred to by the name 'Empty Feelings'.

The new Phlox is a naturally-occurring whole plant mutation of the *Phlox paniculata* cultivar Popeye, not patented. The new Phlox was discovered by the Inventor in a controlled environment in Den Hoorn, The Netherlands, within a population of plants of 'Popeye'. The selection of this new Phlox was based on its lack of typical Phlox flowers. Plants of the cultivar Popeye have typical Phlox flowers whereas plants of the new Phlox do not have typical Phlox flowers and only produce clusters of bract-like structures.

Asexual reproduction of the new cultivar by vegetative cuttings taken at Den Hoorn, The Netherlands since May, 1999, has shown that the unique features of this new Phlox are stable and reproduced true to type in successive generations.

SUMMARY OF THE INVENTION

Plants of the cultivar Empty Feelings have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'Empty Feelings'. These characteristics in combination distinguish 'Empty Feelings' as a new and distinct cultivar:

1. Plants of the new Phlox have an upright plant habit.
2. Plants of the new Phlox have dark green leaves.
3. Inflorescences of plants of the new Phlox do not have typical Phlox flowers with corollas, calyces and reproductive structures; instead inflorescences of plants of the new Phlox consist of clusters of dark red bract-like structures.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Phlox. The photograph comprises a side perspective view of a typical flowering stem of 'Empty Feelings'. The age and environmental conditions of the plants depicted in the drawing are the same as those disclosed in the Detailed Botanical Description.

DETAILED BOTANICAL DESCRIPTION

The following observations, measurements and values describe plants of the new cultivar grown in the field under outdoor conditions during the summer in Den Hoorn, The Netherlands. Plants used in the photographs and the detailed botanical description were about 30 weeks from planting rooted cuttings. Color references are made to The Royal Horticultural Society Colour Chart except where general terms of ordinary dictionary significance are used.

Botanical classification: *Phlox paniculata* cultivar Empty Feelings.

Parentage: Naturally-occurring whole plant mutation of *Phlox paniculata* cultivar Popeye, not patented.

Propagation:
- *Type cutting.*—Vegetative cuttings.
- *Time to produce a rooted cutting.*—Summer: About 20 days at 20° C. Winter: About 35 days at 12° C.
- *Root description.*—Thick, fibrous.

Plant description:
- *Form.*—Upright, conical.
- *Usage.*—Perennial garden plant; cut flower.
- *Crop time.*—From cuttings, about 30 weeks are required to produce fully-grown flowering plants in 1.5-liter containers.
- *Plant height.*—About 80 cm.
- *Area of spread.*—About 35 cm.
- *Vigor.*—Moderately vigorous.
- *Branching habit.*—Freely basal branching; about 18 stems develop per plant during the flowering season with about four panicles per stem.
- *Stems.*—Length: About 80 cm. Diameter: About 2 mm. Internode length: About 6 cm. Texture: Smooth, glabrous. Strength: Strong. Color: 143A.
- *Foliage description.*—Leaves simple, opposite, generally symmetrical, durable and long persisting. Length: About 13.5 cm. Width: About 4.1 cm. Shape: Elliptic to narrowly elliptic. Apex: Acute. Base:

Attenuate. Margin: Serrulate. Texture, both surfaces: Somewhat leathery; glabrous. Venation pattern: Pinnate. Color: Young Foliage, upper surface: 137A to 139A. Young foliage, lower surface: 137C. Mature foliage, upper surface: 137A. Mature foliage, lower surface: 137C. Venation, upper surface: 143C to 144A. Venation, lower surface: 143A. Petiole: Length: About 1 mm. Diameter: About 3 by 2 mm. Texture, both surfaces: Smooth. Color, both surfaces: 143C.

Flower description:

*Flower type and habit.*—Typical Phlox flowers do not develop. Panicles with numerous clusters of bract-like structures. Panicles about 30 cm high and about 20 cm wide. Bract-like structures persistent.

*Natural flowering season.*—"Flowering" continuous during the summer from July to September in Den Hoorn, The Netherlands.

*Quantity.*—Freely "flowering" with about 400 bract-like clusters per flowering stem over the entire "flowering" period.

*Fragrance.*—Not detected.

*"Flower" longevity on the plant and as a cut flower.*—About 14 days.

*"Flower" buds.*—Length: About 1.5 cm. Diameter: About 1 mm. Shape: Ovate. Color: 143B to 143C.

*Bracts-like structures.*—Immature. Quantity/arrangement: About 10 in a cluster. Length: About 1.5 mm. Width: About 0.1 to 0.4 mm. Shape: Linear. Apex: Acuminate. Margin: Entire. Texture, both surfaces: Smooth. Color, both surfaces: 143B to 143C. Mature: Quantity/arrangement: About 10 in a cluster. Length: About 3 to 12 mm. Width: About 1.5 mm. Shape: Linear to narrow subulate. Apex: Acuminate. Margin: Entire. Texture, both surfaces: Smooth. glabrous. Color, both surfaces: 185A to 185B.

*Pedicels.*—Angle: Upright to about 90° from stem. Strength: Strong. Length: About 6 mm. Diameter: About 1.5 mm. Color: 185A to 185B.

Disease/pest resistance: Resistance to pathogens or pests common to Phlox has not been observed.

It is claimed:

1. A new and distinct cultivar of Phlox plant named 'Empty Feelings', as illustrated and described.

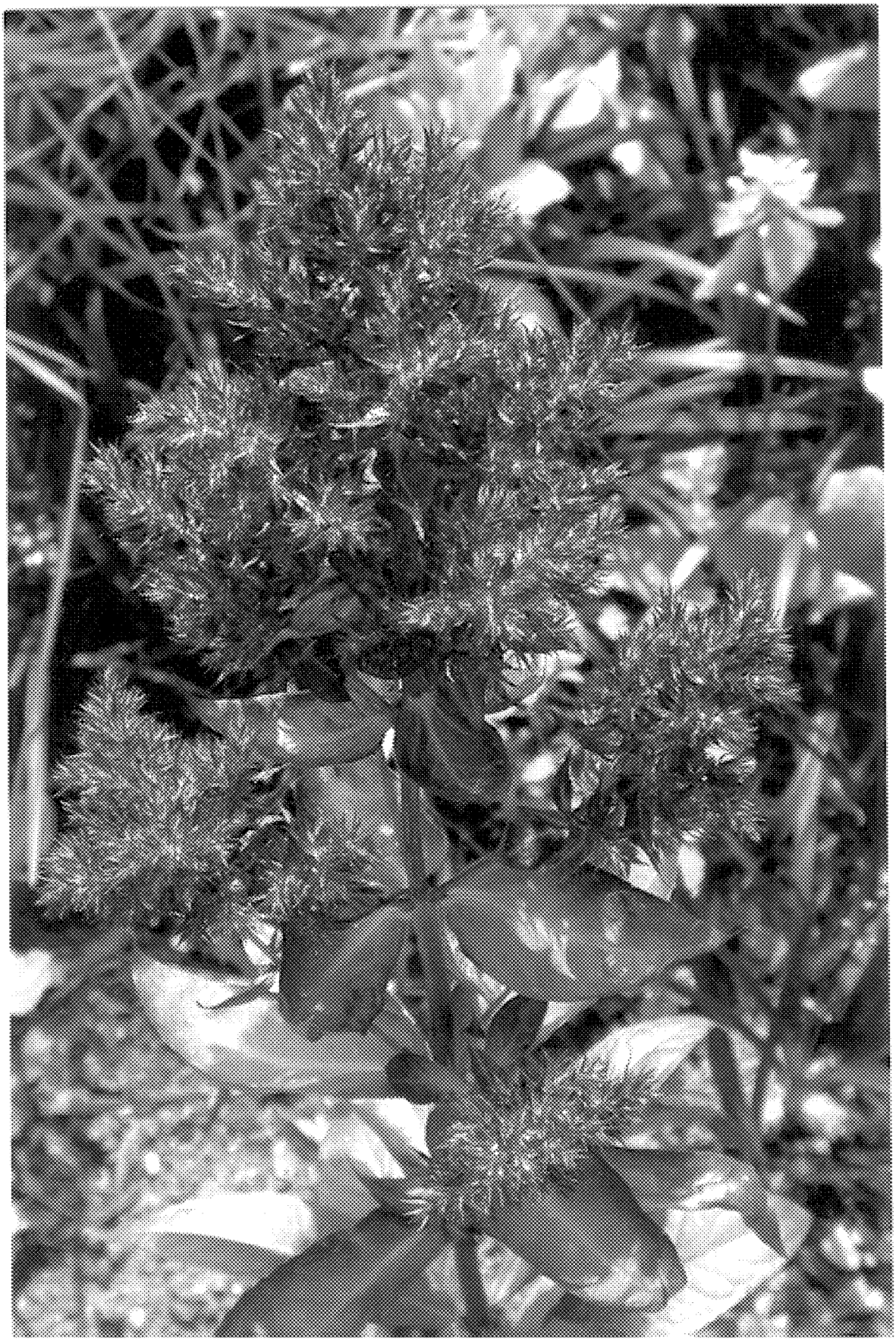

* * * * *